United States Patent
Ning et al.

(10) Patent No.: US 9,486,345 B2
(45) Date of Patent: Nov. 8, 2016

(54) METHODS AND SYSTEMS FOR PLACEMENT OF A STENT ADJACENT AN OSTIUM

(75) Inventors: Kelvin Ning, San Francisco, CA (US); Richard Scott Rader, Wayland, MA (US)

(73) Assignee: Covidien LP, Mansfield, MA (US)

( * ) Notice: Subject to any disclaimer, the term of this patent is extended or adjusted under 35 U.S.C. 154(b) by 2051 days.

(21) Appl. No.: 11/969,021

(22) Filed: Jan. 3, 2008

(65) Prior Publication Data
US 2009/0177259 A1 Jul. 9, 2009

(51) Int. Cl.
*A61F 2/06* (2013.01)
*A61F 2/958* (2013.01)
*A61F 2/954* (2013.01)
*A61F 2/82* (2013.01)

(52) U.S. Cl.
CPC .............. *A61F 2/958* (2013.01); *A61F 2/954* (2013.01); *A61F 2002/821* (2013.01)

(58) Field of Classification Search
CPC .......... A61F 2/95; A61F 2/954; A61F 2/958; A61F 2002/821
USPC ........................................................ 623/1.11
See application file for complete search history.

(56) References Cited

U.S. PATENT DOCUMENTS

| | | | |
|---|---|---|---|
| 5,607,444 A * | 3/1997 | Lam | 606/194 |
| 5,632,762 A * | 5/1997 | Myler | 606/194 |
| 5,749,890 A | 5/1998 | Shaknovich | |
| 7,105,015 B2 | 9/2006 | Goshgarian | |
| 7,147,658 B2 | 12/2006 | Vrba | |
| 2004/0093058 A1 | 5/2004 | Cottone et al. | |
| 2004/0138737 A1* | 7/2004 | Davidson | A61F 2/82 623/1.35 |
| 2005/0197692 A1* | 9/2005 | Pai et al. | 623/2.1 |
| 2006/0058864 A1 | 3/2006 | Schaeffer et al. | |
| 2006/0106455 A1 | 5/2006 | Furst et al. | |
| 2006/0142847 A1* | 6/2006 | Shaknovich | 623/1.24 |
| 2006/0173528 A1* | 8/2006 | Feld et al. | 623/1.15 |
| 2006/0265041 A1 | 11/2006 | Sanati et al. | |
| 2007/0038283 A1* | 2/2007 | Mustapha | A61F 2/856 623/1.11 |
| 2007/0073388 A1 | 3/2007 | Krolik et al. | |

\* cited by examiner

*Primary Examiner* — Diane Yabut

(57) ABSTRACT

The present invention provides for treatment of ostial occlusions through placement of scaffold in a side-branch adjacent the ostium.

15 Claims, 4 Drawing Sheets

METHODS AND SYSTEMS FOR PLACEMENT OF A STENT ADJACENT AN OSTIUM

BACKGROUND OF THE INVENTION

1. Field of the Invention

The present invention relates generally to medical devices and methods and more particularly to methods and devices for placing stents adjacent a vascular ostium in the peripheral vasculature.

The treatment of occlusions near side branches in a patient's vasculature have been problematic. While stents may be used to maintain patency in the main lumen, the ostium of the side branch is often occluded.

Congenital narrowing of the left common iliac vein due to pressure from the overlying artery is called May-Thurner syndrome and can lead to deep vein thrombosis of the left leg. The blood coming from the legs flows through the deep veins of the legs and the pelvis into the big abdominal vein and then to the heart Normally, the artery which runs to the right leg (right common iliac artery) lies on top of the vein coming from the left leg (left common iliac vein). This close proximity leads, in some people, to pressure of the artery onto the vein and to varying degrees of narrowing of the vein which is characteristic of May-Thurner syndrome. Mild and moderate degrees of narrowing are typically asymptomatic. More severe degrees can lead to obstruction of blood flow from the leg and thus to leg swelling and pain. The narrowed vein can also clot, resulting in left leg deep vein thrombosis (DVT). Several surgical treatment strategies have been employed in the past including venous bypass surgery of the narrowed area, cutting of the iliac artery and repositioning of the artery behind the iliac vein, and construction of a tissue sling or flap to lift it off the iliac vein, but none have fully addressed the condition.

Thus, it is desirable to provide more effective and less invasive methods and systems for treating an occluded ostium in the peripheral vasculature, particularly in patients suffering from May-Thurner syndrome.

2. Description of the Background Art

Flared and other stents for positioning in bifurcation are described in US2007/0073388; US2007/0038283; US2006/0265041; US2006/0106455; US2006/0058864; US2004/0093058; U.S. Pat. No. 7,147,658; U.S. Pat. No. 7,105,015; U.S. Pat. No. 5,749,890; and U.S. Pat. No. 5,632,762.

BRIEF SUMMARY OF THE INVENTION

The present invention provides methods and systems for placement of a scaffold, such as an expandable stent, in side branch vessels adjacent to an ostium in a main branch. The expandable member may be a stent, such as a balloon or self-expanding stent, and can be used for treating venous occlusions in patients suffering from May-Thurner syndrome. The stenosis or occlusion may occur at an ostium or at a bifurcation, for example, where bifurcation occurs and a branch vessel continues and extends from the main ostium. By way of example, such ostium is in the peripheral vein such as the inferior vena cava in the iliac vein.

It is advantageous to treat an occlusion at the ostium with minimal or no disruption to the flow of blood from the side branch to the main branch. Treatment of side branches in the venous vasculature, however, is complicated by the direction of blood which flow is opposite to that of arterial flow. In particular, it is difficult to fluoroscopically visualize the ostium when blood flows from a collateral branch as it does on the venous side. Stenting the iliac vein at the ostium is particularly difficult. While the present invention is particularly useful for treating the venous system, it should not be read as limitation of the present invention.

The present invention, among other things, provides for methods for enhancing the treatment of an occluded ostium by placement of a stent (or other suitable scaffolds) via access through a side branch vessel which is adjacent to the ostium without or minimizing the obstruction of blood flow and/or enhancing visualization.

In an embodiment, a stent is delivered to a side branch which is adjacent to an ostium such as the iliac vein os in the venous vasculature. The method includes advancing a distal end of a catheter through the side branch vessel and into a lumen of the main branch vessel. An anchor on the distal end of the catheter is inflated or otherwise expanded in the main vessel lumen. The catheter is pulled back, and the expanded anchor is seated in the ostium. An expandable scaffold, such as a stent or graft, is carried on a portion of the catheter proximal, preferably immediately proximal, to the expanded anchor. The stent may be expanded and positioned in the branch vessel adjacent the ostium relying on the anchor for proper positioning.

The anchor may be any suitable anchor, such as inflatable anchors including inflatable balloons, and mechanically expandable anchors including mallecotts. In an embodiment where the anchor comprises balloon-expandable anchor, the method further comprises inflating the balloon. Similarly, the stent may be a balloon-expandable stent which is carried by the same balloon wherein the stent is disposed on at least a portion thereof when the balloon is in the side branch, or a second balloon. The stent is expanded when the balloon is expanded. If the stent is a self-expanding stent, it is constrained by a retractable cover so that it resiliently expands at the desired location in the side branch. The side-branch vessels may be in any area of peripheral vasculature which emanates from an ostium. By way of example such vessel may be in the venous vasculature, such as in an iliac vein where the ostium is located at inferior vena cava.

In some embodiments, the method may further comprise rotationally orienting the stent within the branch vessel. In an embodiment, including features of the present invention, the stent has a beveled distal end (i.e., disposed at an angle relative to a straight or transverse cut end). Rotation allows for the alignment of the beveled end of the stent which is in the side branch of the ostium prior to expansion of the stent. In an embodiment, the beveled edge of the stent ends immediately before the edge of the ostium, to minimize the possibility of the entry of the stent into the main branch.

The present invention also includes an exemplary stent delivery system, embodying features of the present invention. The system includes, a catheter with a body, proximal and distal ends. An anchor configured to seat in an ostium is provided on the catheter body. An expandable stent is disposed on the catheter body, proximal, preferably immediately proximal, to the expandable anchor. The stent is expandable in a branch vessel adjacent to an ostium where the anchor is disposed in a main vessel seated in the ostium.

It should be noted that the inflatable anchor may be of any suitable anchors such as inflatable anchors including those inflatable by balloons. Similarly, the stent may be a balloon-expandable stent which is carried, at least along a portion of the expandable balloon when the balloon has been withdrawn from the main branch, or by a second balloon, as noted above. In an embodiment, the stent is a self-expanding stent. The self-expanding stent is radially constrained on the catheter body by a retractable cover. In an embodiment, the distal end of the stent is beveled to align with the ostium after the stent is expanded.

The present invention further provides a stent delivery system, including in part, a catheter body, and an expandable anchor disposed on the catheter body near a distal end. The anchor is adapted to seat in an ostium. In an embodiment, the anchor is an expandable balloon. An expandable stent (balloon expandable or self-expanding) is disposed on the catheter body, proximal, preferably immediately proximal, to the expandable anchor. The stent may be expanded in a branch vessel adjacent to the ostium when the anchor is disposed in a main vessel seated in the ostium. In an exemplary embodiment, the stent may be self-expanding which is radially constrained on the catheter by a retractable cover until it is time to be expanded.

Either or both the stent and the catheter may include at least one orientation marker which permits rotational alignment under fluoroscopic imaging prior to expansion of the stent. Furthermore, the stent may be tapered in the proximal direction. In one exemplary system, the stent delivery system, either or both the catheter and the stent includes an orientation marker which permits rotational alignment under fluoroscopic imaging prior to expansion of the stent. In another exemplary system, the stent is tapered in the proximal direction. This proximal tapering minimizes the overexpansion of the venous vessel.

DETAILED DESCRIPTION OF THE INVENTION

Figure 1:
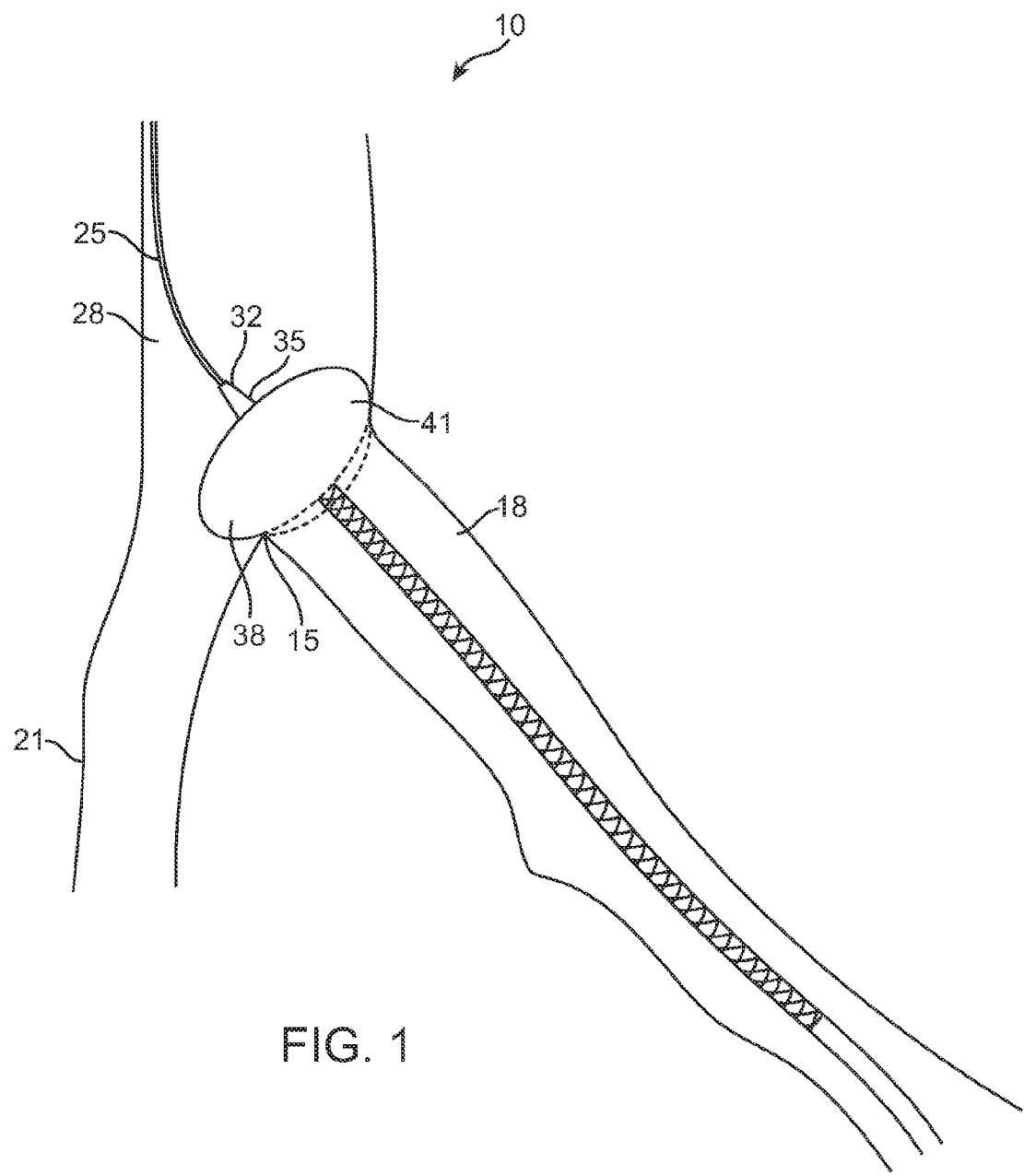
FIG. 1 illustrates an exemplary embodiment including features of the present invention, where a guidewire has been placed in the main branch.

Now referring to FIGS. 1-4, a method, for placing a stent in aside branch adjacent to an ostium in a main branch vessel is described. An ostium 15 of a portion of a vasculature 10 is shown, with side-branches 18 and 21. The ostium at the main branch may be bifurcating into a vein such as an iliac vein 18. A guidewire 25 passes through the side branch 18 into the main branch 28 where the side branch emanates from the ostium. A distal end 32 of a catheter 35, as known in the art, which is configured in size and shape for the application, is advanced over the guidewire. An anchor 38, such as a balloon 41, is disposed over the distal end of the catheter. The expandable member, as for example the balloon 41, is expanded using methods generally known in the art into the larger main branch 28. The catheter is pulled back proximally to seat the expanded anchor in the ostium 15.

Figure 2:
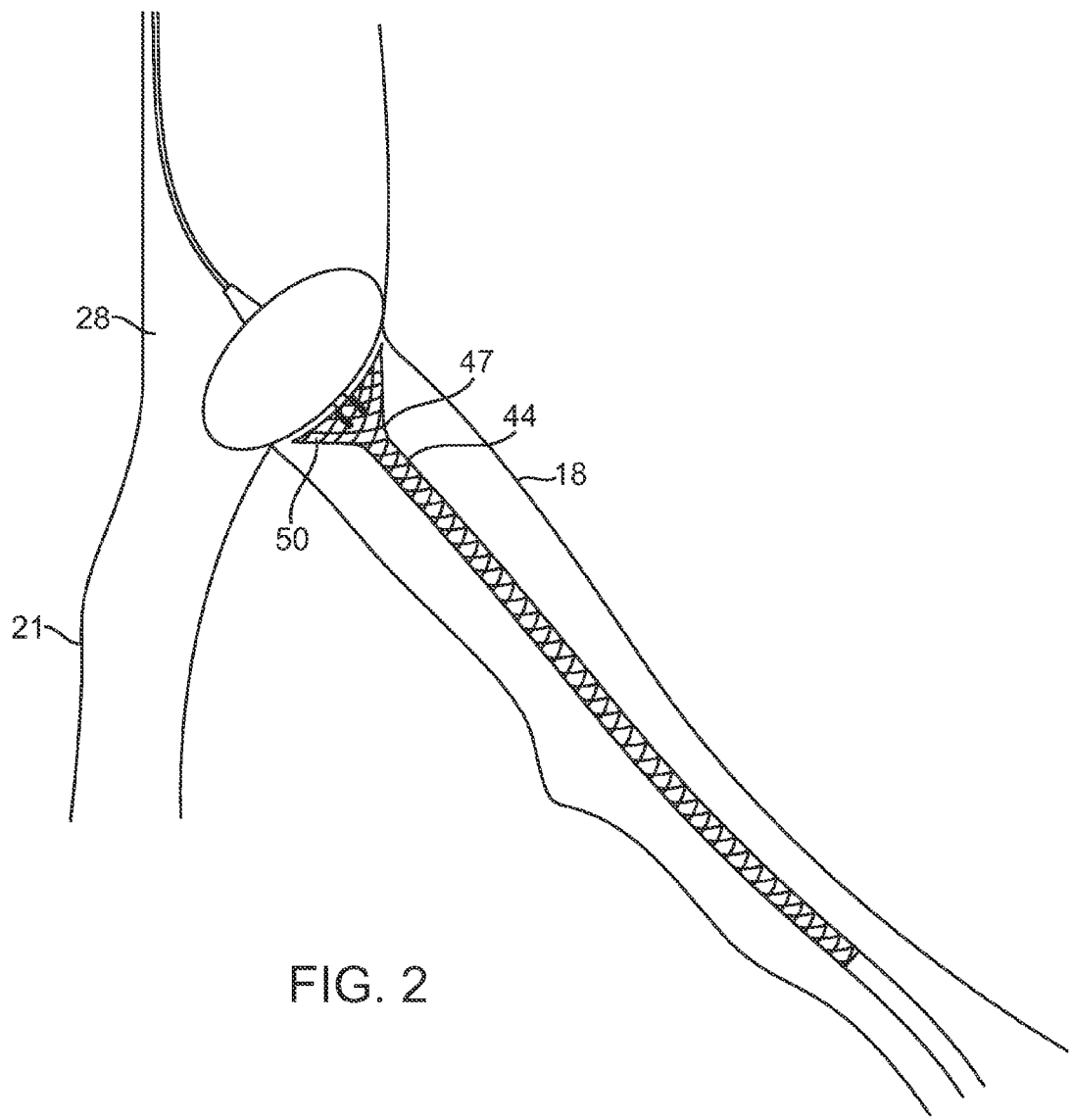
FIG. 2 illustrates an exemplary embodiment including features of the present invention, where a guidewire has traversed the ostium with the distal end of the catheter over the guidewire.

Referring to FIG. 2, the balloon-expandable stent 44, is expanded within the side-branch 18 with a distal end 47 of the stent being disposed immediately proximal to the ostium. Optionally, the distal end 47 of the stent 44 may be beveled 50 to align the stent with the ostium prior to the expansion of the stent in the side branch. The stent may be rotationally oriented to allow for such alignment. Furthermore, optionally radiopaque markers may be placed on or about the beveled edge 50 of the stent for correct orientation. Preferably, the marker is kept to a single marker for correct resolution.

Figure 3:
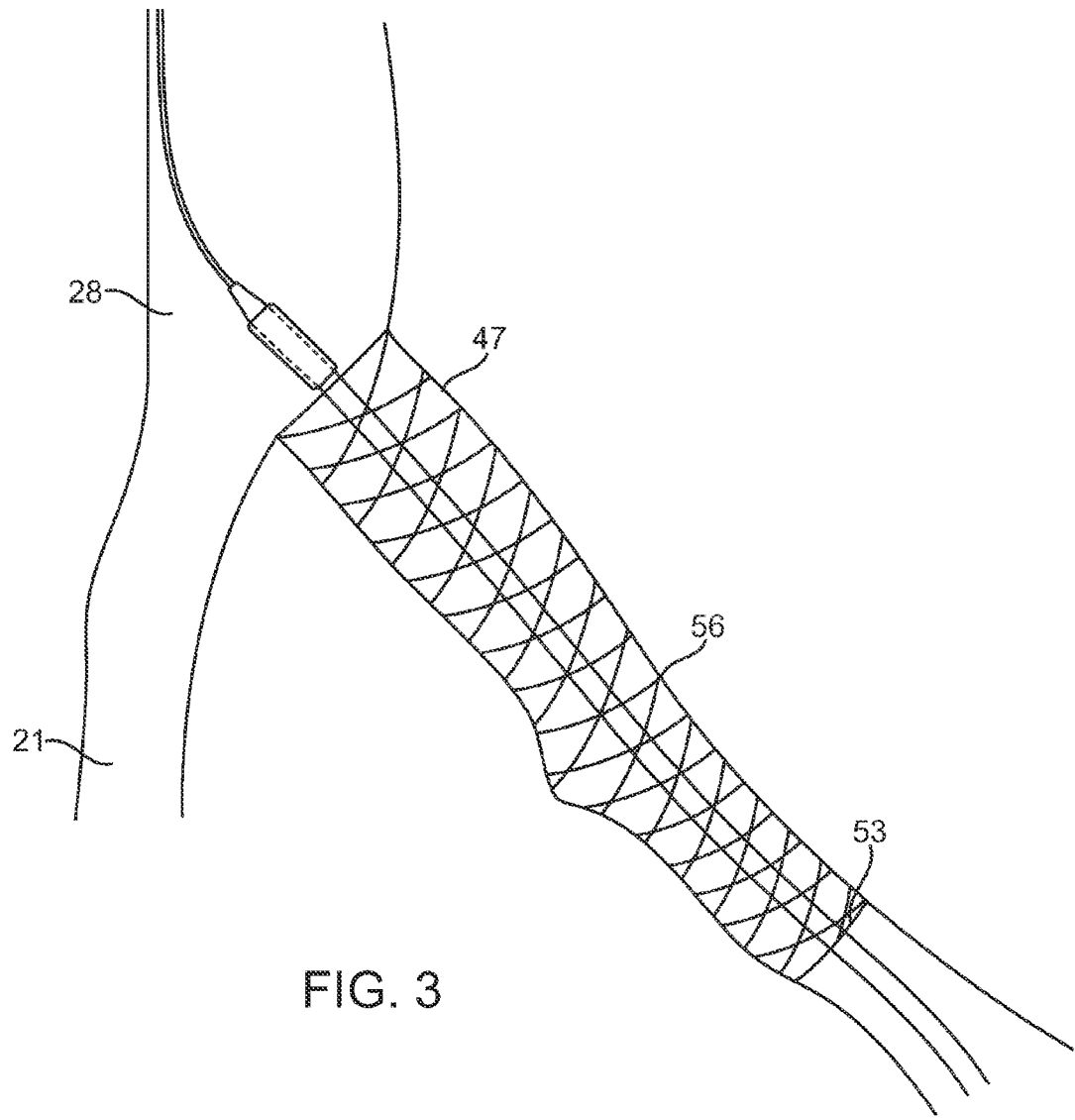
FIG. 3 illustrates an exemplary embodiment including features of the present invention, with the stent in an expanded stent in the side-branch.

Now referring to FIG. 3, the stent may be tapered in the proximal direction of the stent. By way of example, as shown, the proximal end 53 of the stent may have a diameter of approximately 8 to 12 mm, normally 10 mm, with the diameter of the intermediate area 56 at about 12-14 mm, normally about 13 mm, and the distal end 47 of the stent being from 12 to 18 mm, generally from 16-18 mm, normally 16 mm.

Figure 4:
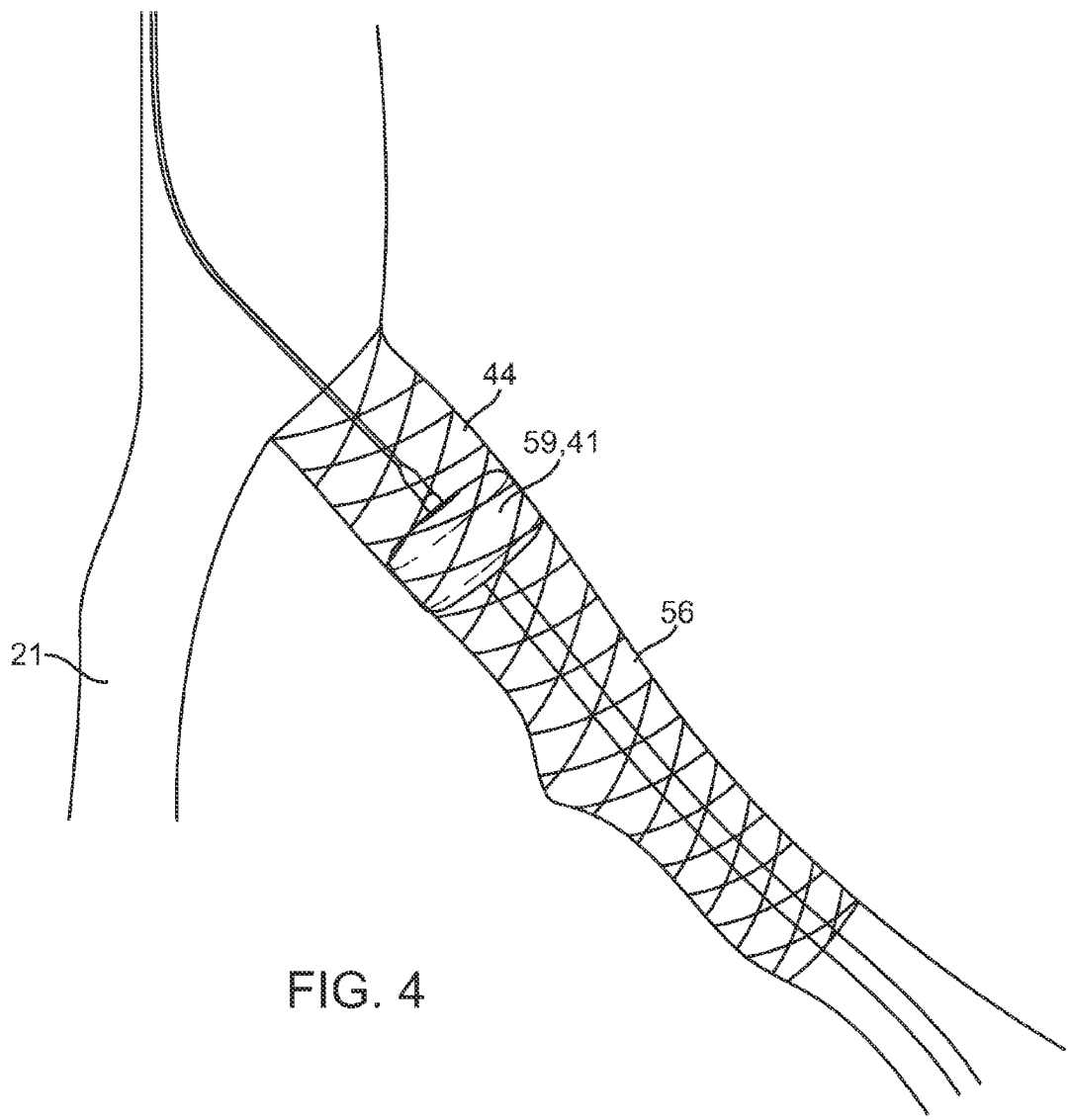
FIG. 4 illustrates an exemplary embodiment including features of the present invention, with the stent expanded in the side-branch using a balloon-expandable stent.

Referring to FIG. 4, a balloon 59 (or the same balloon 41 as used earlier but now in a less expanded position) is used to expand the stent. The expandable stent may be further expanded to assist in tacking the stent to the wall of the side branch. The balloon for expanding the stent in the side-branch is thereafter deflated and withdrawn as is commonly known in the industry.

The present invention is also directed to systems including a catheter having a catheter body and proximal and distal ends. The system, further includes an expandable anchor (as described above) for disposing on the catheter body near the distal end. The anchor is adapted to seat in an ostium. An expandable stent (as described above) is disposed on the catheter body, proximal, preferably immediately proximal, to the expandable anchor. The stent is configured to be expandable in a branch vessel adjacent to the ostium when the anchor is seated the main vessel of the ostium.

The expandable anchor may be of any suitable expandable anchor such as one expandable by a balloon. Similarly, the expandable stent may be a balloon-expandable stent or one which is self-expandable with a retractable cover maintaining it in the un-expanded position until it is time to expand the stent.

In an embodiment of the system, either or both, the catheter and the stent include an orientation marker which aids in rotational alignment under fluoroscopic imaging prior to expansion of the stent. The stent, as described, earlier, may be tapered in the proximal direction.

It should be noted that, the stent delivery system may include any one or more features of the device/method described above.

What is claimed is:

1. A method for delivering a stent to a side branch vessel adjacent to an ostium in a main branch vessel, said method comprising:

advancing a distal end of a catheter through a lumen of the side branch vessel and into a lumen of the main branch vessel until an expandable stent carried on the catheter proximal to the distal end of the catheter is located in the lumen of the side branch vessel adjacent the ostium;

expanding, to an expanded state, an anchor on the distal end of the catheter while the anchor is substantially located in the main vessel lumen;

pulling the catheter proximally to seat the expanded anchor in the ostium so that a portion of the expanded anchor seats in the ostium and extends through the ostium and expands a distal end of the stent within the lumen of the side branch vessel adjacent the ostium; and expanding the stent carried on a portion of the catheter proximal to the expanded anchor so that the expanded stent is positioned in the branch vessel adjacent to the ostium.

2. The method as in claim 1, wherein the vessels are in the venous vasculature.

3. The method as in claim 2, wherein the stent is expanded in an iliac vein and the ostium is in the inferior vena cava.

4. The method as in claim 1, wherein expanding the anchor comprises inflating a balloon.

5. The method as in claim 1, wherein expanding the stent comprises inflating a balloon which carries the stent along at least a portion thereof.

6. The method as in claim 1, wherein expanding the stent comprises releasing the stent from constraint so that it resiliently expands.

7. The method as in claim 1, further comprising rotationally orienting the stent within the side branch vessel to align a beveled end of the stent with the ostium prior to expansion of the stent.

8. The method as in claim 1, wherein the step of expanding the stent is performed while the anchor is in the expanded state.

9. The method as in claim 1, wherein the expanded stent does not extend past the ostium.

10. A method for delivering a stent to a side branch vessel adjacent to an ostium in a main branch vessel, said method comprising:

advancing a distal end of a catheter through a lumen of the side branch vessel and into a lumen of the main branch vessel until an expandable stent carried on the catheter proximal to the distal end of the catheter is located in the lumen of the side branch vessel adjacent the ostium;

expanding, to a greater expanded state, an anchor on the distal end of the catheter while the anchor is substantially located in the main vessel lumen;

pulling the catheter proximally to seat the expanded anchor in the ostium;

partially shrinking the anchor to a lesser expanded state;

pulling the catheter further proximally to locate the anchor in its lesser expanded state to a position within the stent: and partially expanding the anchor within the stent from the lesser expanded state, thereby expanding the stent carried proximal to the distal end of the catheter so that the expanded stent is tacked to a side wall of the branch vessel adjacent to the ostium and so that a distal end of the stent is expanded within the lumen of the side branch vessel adjacent the ostium.

11. The method as in claim 10, wherein the vessels are in the venous vasculature.

12. The method as in claim 11, wherein the stent is expanded in an iliac vein and the ostium is in inferior vena cava.

13. The method as in claim 10, wherein expanding the anchor comprises inflating a balloon.

14. The method as in claim 10, further comprising rotationally orienting the stent within side the branch vessel to align a beveled end of the stent with the ostium prior to expansion of the stent.

15. The method as in claim 10, wherein the expanded stent does not extend past the ostium.

* * * * *